United States Patent
Osterholt et al.

(10) Patent No.: US 7,385,092 B2
(45) Date of Patent: Jun. 10, 2008

(54) PROCESS FOR PREPARING ALKANEDIOLS AND ALKANETRIOLS HAVING A VICINAL DIOL GROUP

(75) Inventors: Clemens Osterholt, Dorsten (DE); Volker Brehme, Münster (DE); Thomas Kübelbäck, Dülmen (DE); Günther Köhler, Marl (DE)

(73) Assignee: Degussa AG, Duesseldorf (DE)

( * ) Notice: Subject to any disclaimer, the term of this patent is extended or adjusted under 35 U.S.C. 154(b) by 378 days.

(21) Appl. No.: 11/300,289

(22) Filed: Dec. 15, 2005

(65) Prior Publication Data

US 2006/0161025 A1    Jul. 20, 2006

(30) Foreign Application Priority Data

Dec. 15, 2004    (DE) .................. 10 2004 060 541

(51) Int. Cl.
*C07C 29/128* (2006.01)

(52) U.S. Cl. .................................. 568/858

(58) Field of Classification Search ........... 568/858
See application file for complete search history.

(56) References Cited

U.S. PATENT DOCUMENTS

| | | | |
|---|---|---|---|
| 2,739,173 A | 3/1956 | Corey et al. | |
| 3,776,948 A | 12/1973 | Kleemann et al. | |
| 4,339,616 A | 7/1982 | Rutzen et al. | |
| 4,479,021 A | 10/1984 | Issler et al. | |
| 4,605,795 A | 8/1986 | Siegmeier et al. | |
| 4,626,603 A | 12/1986 | Siegmeier et al. | |
| 4,762,954 A | 8/1988 | Siegmeier et al. | |
| 4,801,759 A | 1/1989 | Siegmeier et al. | |
| 5,030,771 A | 7/1991 | Fuhrmann et al. | |
| 5,426,249 A | 6/1995 | Haas et al. | |
| 6,281,394 B1 | 8/2001 | Oftring et al. | |
| 6,313,356 B1 | 11/2001 | Kohler et al. | |
| 2006/0161025 A1 | 7/2006 | Osterholt et al. | |

FOREIGN PATENT DOCUMENTS

| | | |
|---|---|---|
| DE | 1944120 | 4/1971 |
| DE | 29 37 840 A1 | 4/1981 |
| DE | 32 29 084 A1 | 2/1984 |
| DE | 197 43 015 A | 4/1999 |
| DE | 197 43 015 A1 | 4/1999 |
| DE | 199 29 196 A1 | 12/2000 |
| EP | 0 025 890 B1 | 4/1983 |
| EP | 0 141 775 A | 5/1985 |
| EP | 0 141 775 A1 | 5/1985 |
| GB | 2 145 076 A | 3/1985 |
| JP | 11-193225 | 7/1999 |
| JP | 2001-48720 | 2/2001 |
| JP | 2003-342146 | 12/2003 |
| WO | WO 01/89466 A1 | 11/2001 |

OTHER PUBLICATIONS

U.S. Appl. No. 06/187,944, filed Sep. 16, 1980, Gerhard et al.
U.S. Appl. No. 11/843,384, filed Aug. 22, 2007, Krimmer et al.
Hydroxulation and Epoxidaiton of Some 1-Olefins with per-acids, Daniel Swern, et al.; J. Am. Chem. Soc. 68 (1946), pp. 1504-1507.

*Primary Examiner*—Elvis O Price
(74) *Attorney, Agent, or Firm*—Oblon, Spivak, McClelland, Maier & Neustadt, P.C.

(57) ABSTRACT

A process for preparing diols or triols made up of
  a1) reacting at least one monoolefin having 4 to 20 carbon atoms with hydrogen peroxide and formic acid in the presence of water to form a mixture or
  a2) reacting at least one monoolefin alcohol having 4 to 20 carbon atoms first with formic acid, and then reacting the product formed thereby with hydrogen peroxide in the presence of water to form a mixture,
  b) removing, by distillation, the water and formic acid from the mixture obtained in a1) or a2),
  c) reacting the mixture obtained from b) with an aliphatic alcohol in the presence of a sulfonic acid to form the diol or triol and at least one formic ester by-product, and
  d) optionally removing, by distillation, the at least one formic ester by-product formed together with any residual at least one aliphatic $C_1$-$C_4$-alcohol to isolate the diol or triol.

23 Claims, No Drawings though it is not necessary to do so, the reaction mixture can also be distilled first to remove low-boiling reaction constituents and only then be subjected to thermal treatment.

PROCESS FOR PREPARING ALKANEDIOLS AND ALKANETRIOLS HAVING A VICINAL DIOL GROUP

CROSS REFERENCE TO RELATED APPLICATIONS

This application claims priority to German Patent Application No. 102004060541.6, filed on Dec. 15, 2004, which is incorporated herein by reference in its entirety.

BACKGROUND OF THE INVENTION

Field of the Invention

The present invention describes a process for preparing diols and triols by reacting respectively alkenes and alkenols with formic acid and aqueous hydrogen peroxide solution. The initially formed intermediate formates are subsequentely converted by transesterification into the corresponding diols and triols.

DISCUSSION OF THE BACKGROUND

The preparation of 1,2-diols by the reaction of 1-olefins with formic acid and hydrogen peroxide, at a temperature of 40° C., followed by subsequent hydrolysis, is disclosed in the literature (D. Swern et al. in J. Am. Chem. Soc. 68 (1946), pages 1504 to 1507).

DE 19 44 120 describes a process for preparing glycerol from allyl acetate and aqueous peracetic acid. After formation of glyceryl acetate, the low boiling reaction constituents (i.e., unreacted allyl acetate, water and acetic acid) are removed by distillation. The remaining glyceryl acetate (mainly monoacetin) is then mixed with p-toluenesulfonic acid and transesterified with methanol. After transesterification, the catalyst (i.e., p-toluenesulfonic acid) is removed from the reaction mixture by means of a basic ion exchanger, and the crude product is worked up by distillation.

Disadvantages associated with this method are: 1) the use of the toxic methanol as transesterification agent, and 2) the additional workup step of treatment with a basic ion exchanger. The requirement for treatment with a basic ion exchanger results in a considerable increase in complexity, especially in an industrial process. Additionally, the oxidation reaction with acetic acid and hydrogen peroxide proceeds more slowly than with formic acid and hydrogen peroxide.

U.S. Pat. No. 2,739 173 describes a process for preparing glycerol from allyl alcohol and aqueous peracetic acid. In this process, an initial reaction mixture, which is produced from glyceryl formates, is subsequently distilled to remove aqueous formic acid. Methanol and sulfuric acid are then added to the distillation residue, and the resulting mixture is then heated to produce glycerol and methyl formate. The ester resulting from this process is subsequently distilled off and the sulfuric acid is then neutralized with NaOH. Excess methanol is then distilled off, and the glycerol is isolated from the residue by distillation.

The disadvantages associated with this are again the use of toxic methanol as the transesterification agent, the additional workup step of neutralization of the sulfuric acid with NaOH, and the production of a salt associated therewith. Further, a particular disadvantage is that the sulfuric acid catalyst has an adverse effect on the odor quality of the target product, especially when alkenols having more than 3 C atoms are used instead of allyl alcohol.

DE 32 29 084 describes a process for preparing vicinal diols and formates thereof. The formates formed in the reaction of olefins with formic acid and hydrogen peroxide are converted, via decarbonylation with catalytic amounts of alcoholate, into the corresponding diols.

The disadvantages in this case are: 1) that the use and handling of alcoholates in an industrial process is complicated, 2) the need to use high reactor temperatures of 150 to 180° C. for decarbonylation, 3) the impairment of the odor quality of the target products caused by the high decarbonylation reaction temperatures, and 4) the production of toxic carbon monoxide.

DE 29 37 840 describes a process for the hydroxylation of aliphatic mono- and diolefins. Mention is made, inter alia, of the reaction of monoolefins, which are unsubstituted or substituted by one or two hydroxy groups, with formic acid and hydrogen peroxide. To break down the $H_2O_2$ after the reaction, the crude product is normally passed over a fixed bed (fixed-bed platinum catalyst). The formates formed as intermediates, which are not specifically mentioned in the patent, are hydrolyzed with water or NaOH.

The disadvantages of this process are: 1) the additional workup stage required to break down $H_2O_2$ on a special fixed-bed catalyst, 2) the requirement for the use of NaOH for hydrolysis where diols having $\geq 5$ C atoms are prepared, 3) the need to extract the product with a solvent, which requires additional effort and the use of auxiliaries, and 4) the production of a salt.

EP 0 141 775 describes a continuous process for preparing 1,2-alkanediols. The process is carried out by reacting 1,2-olefins with formic acid and hydrogen peroxide to form formates, hydrolyzing the formates in a multistage process employing concentrated aqueous alkali solutions, extracting the reaction product with an organic solvent, and isolating the product from the extract by distilling off the solvent.

The disadvantages in this continuous process are: 1) the need to use solvents, and 2) the formation of stoichiometric amounts of salts of formic acid, the removal and disposal of which is complex.

GB 2 145 076 also describes a continuous process for preparing 1,2-alkanediols. The process is carried out by reacting 1,2-olefins with hydrogen peroxide and formic acid to form esters, hydrolyzing the resulting esters with 25% strength sodium hydroxide solution, and distilling the resulting organic phase to obtain the product.

Disadvantages of this process include: 1) formation of formic acid salts which must be removed and disposed of in a complicated manner, and 2) residual amounts of sodium formate remaining in the organic phase which promote decomposition of the diols or triols during the subsequent workup by distillation so that an impure product may result and the impure product may comprise malodorous components.

DE 197 43 015 describes a multi-step process for preparing vicinal diols or polyols. In the first step of this process, formation of formyl esters of diols or polyols by oxidation with hydrogen peroxide/formic acid is accompanied by formation of an organic and an aqueous phase. According to Example 1, the aqueous phase contains excess formic acid while the organic phase contains 14% water, formyl esters, and 1,2-diols. In the next step, the water-containing organic phase, after removal of the aqueous phase by phase separation, or, alternatively, the complete reaction product, without removal of the aqueous phase—as in Example 3—undergoes thermal treatment after addition of sulfuric acid and methanol. During thermal treatment hydrolysis or methanolysis of the formyl esters of the diols or polyols occurs. In the final step, methyl formate, methanol and water are distilled out together as azeotrope under atmospheric pressure. Following distillation, the vicinal diols or polyols remain behind as a residue.

Disadvantages of this process include: 1) the transesterification with methanol takes place, in each case, in the presence of water and excess formic acid, thereby resulting in the formation of methyl formate and increased methanol consumption, 2) the distillation results in a ternary mixture of methanol, water and methyl formate, which requires elaborate separation for the purpose of recycling, 3) the high temperature in the oxidation reaction results in increased decomposition of, and therefore increased consumption of, hydrogen peroxide (it is worth noting that a reduction in the temperature would lead to higher residual peroxide contents which would lead to both increased safety risks and subsequent hydrolysis/transesterification, so that this route is prohibited), 4) the transesterification and hydrolysis with methanol in the presence of formic acid and water and sulfuric acid leads to a target product having an unpleasant odor so that diols or triols prepared by such processes are completely unsuitable for many areas of application (e.g. in cosmetics), 5) the use of methanol carries the inherent liability of methanol toxicity, 6) if the diols or triols formed are to be used as intermediates for the cosmetics industry, additional purification is required to remove the contaminating methanol, and 7) if the reaction is run without a strongly acidic catalyst, long reaction times and increased formation of byproducts and/or malodorous components result.

DE 199 29 196 describes a process for preparing water-, acid- and odor-free vicinal diols, in which oxidation of the olefin with hydrogen peroxide/formic acid or acetic acid and addition of a solvent are followed by removal of water and formic acid by distillation as a ternary azeotrope. The remaining mixture, which contains the formyl esters of the diols, undergoes alkaline hydrolysis with aqueous sodium hydroxide solution or sodium carbonate solution, in amounts which are approximately stoichiometric in relation to the ester groups, and subsequently the water is removed by azeotropic distillation after addition of a further entrainer (such as toluene). The sodium formate which precipitates during this step is filtered off. In another variant, the toluene-containing hydrolysis solution is neutralized with HCl, and the salt which is then formed is removed. Finally, the remaining toluene phase is concentrated and the diol is isolated.

Despite the statement in the title that the process leads to odor-free diol products, the final products of all the indicated examples are not odor-free but have, for example, a fruity or fatty-aldehydic odor (Example 2). The Applicants have been able to confirm in their own experiments that products with unwanted odor notes are obtained upon alkaline hydrolysis of the intermediate diol formic esters. In addition, the process of DE 199 29 196 is very elaborate and leads, like other processes of this type, to unwanted salt loads.

All the processes known in the prior art have the disadvantages of either being very technically complicated or that they lead to products of insufficient purity, in particular products that have disadvantageous odor properties.

Thus, there remains a need for a simple, high-yielding process that produces, on an industrial scale, vicinal vicinal alkanediols and alkanetriols that lack malodorous impurities.

SUMMARY OF THE INVENTION

Accordingly, it is one object of the present invention to provide a process which is as simple as possible and practicable on the semi-industrial and industrial scale for preparing vicinal alkanediol(s) and alkanetriol(s).

It is another object of the present invention to provide a process for preparing vicinal alkanediol(s) and alkanetriol(s) where the process has short reaction times.

It is a further object of the present invention to provide a process for preparing vicinal alkanediol(s) and alkanetriol(s) that has high space-time yields.

It is an additional object of the present invention to provide a process for preparing vicinal alkanediol(s) and alkanetriol(s) that complies with safety requirements in a sample manner.

It is another object of the present invention to provide a process for preparing vicinal alkanediol(s) and alkanetriol(s) that minimizes losses of auxiliaries such as alcohol or acid.

It is a further object of the present invention to provide a process for preparing vicinal alkanediol(s) and alkanetriol(s) that are essentially free of disadvantageous odors.

It is an additional object of the present invention to provide a process for preparing vicinal alkanediol(s) and alkanetriol(s) with high purities.

It is another object of the present invention to provide a process for preparing vicinal alkanediol(s) and alkanetriol(s) that involves a simple distillative workup.

These and other objects, which will become apparent during the following detailed description, have been achieved by the inventors' discovery that vicinal alkanediol(s) and alkanetriol(s) can be prepared by a process comprising: 1) oxidizing at least one monoolefin and/or monoolefin alcohol with one or more oxidants in water, 2) removing the water, and optionally formic acid, by distillation, 3) treating the oxidized monoolefin or oxidized monoolefin alcohol with at least one $C_1$-$C_4$-alcohol in the presence of at least one arylsulfonic, at least one alkylsulfonic acid, or a combination thereof, and 4) removing reaction by-products via distillation to isolate the at least one vicinal alkanediol(s) and alkanetriol(s), wherein 3)-4) may be performed separately or in combination.

DETAILED DESCRIPTION OF THE PREFERRED EMBODIMENTS

Thus, in a first embodiment, the present invention provides for a novel process for preparing vicinal alkanediol(s) and alkanetriol(s) comprising a1) reacting appropriate monoolefin(s) having 4 to 20 carbon atoms with hydrogen peroxide and formic acid in the presence of water or a2) first reacting appropriate monoolefin alcohol(s) having 4 to 20 carbon atoms with formic acid and subsequently reacting the product formed thereby with hydrogen peroxide in the presence of water, b) removing water and formic acid from the mixture obtained in a1) or a2) by distillation, c) reacting the mixture obtained from b) with at least one aliphatic $C_1$-$C_4$-alcohol in the presence of at least one arylsulfonic acid of the formula $R_n Ar$—$SO_3H$, at least one $C_6$-$C_{16}$-alkylsulfonic acid, or a combination thereof, wherein in the at least one arylsulfonic acid of the formula $R_n Ar$—$SO_3H$, R may be identical or different and is a linear or a branched $C_1$- to $C_{19}$-alkyl radical, a fluorine or a chlorine atom, wherein Ar is a phenyl, naphthyl, anthryl or a phenanthryl radical, and wherein n can be 0, 1, 2 or 3, and d) removal by distillation of the formic ester formed in c) together with the at least one aliphatic $C_1$-$C_4$ alcohol which is still present, where appropriate, from the reaction mixture, wherein c) and d) may be carried out successively or simultaneously, to provide vicinal alkanediol(s) and alkanetriol(s) of high purity, which are essentially free of disadvantageous odor properties, in very good yields, and thus overcome the disadvantages of known preparation processes.

The result achieved by the invention is surprising because DE 197 43 015 discloses only the use of strong acids (such as sulfuric acid or hydrofluoric acid) as catalysts in the methanolysis reaction of alkanediol formates to alkanediols (column 5, lines 60 to 64).

The use of sulfuric acid in the methanolysis reaction is not ideal because the products produced thereby have disadvantageous odor properties.

Further, another catalyst mentioned in DE 197 43 015, hydrofluoric acid, has many disadvantages. Hydrofluoric acid, with its combination of volatility, corrosiveness, and toxicity, entails a higher risk in manufacture and thus a disproportionately large additional expenditure on safety would be necessary during operation.

Other strong inorganic acids such as HCl or organic acids such as acetic acid lead to a reaction rate which is too low, so that disproportionately high temperatures would have to be used, thereby resulting in an increase in the formation of byproducts and odor.

Complete omission of acid always leads, undesirably, to distinctly longer reaction times of, for example, 17 to 18 hours as in the hydrolysis reaction in Example 3 or 7 in DE 197 43 015. In addition, it is necessary to use correspondingly higher temperatures, the use of which results in the previously mentioned disadvantageous consequences.

Although p-toluenesulfonic acid is known in principle as acidic catalyst for esterification reactions, it was by no means possible to expect the inventive effect of achieving odor-free products by the process as described above and claimed in claim 1, in which arylsulfonic acids or higher alkylsulfonic acids mentioned are used as transesterification catalyst.

Further, the distillative removal of water and formic acid in b) results in a distinct reduction in the alcohol consumption in the subsequent transesterification in c). Formation of alkyl formate is likewise reduced, thus reducing the complexity of the process in c).

The elaborate separation of a ternary mixture of water, methanol and formic ester, which are initially distilled out as azeotrope according to DE 197 43 015, and the chemical cleavage of the additionally formed methyl formate back to methanol and formic acid, are also omitted. The formed aqueous formic acid, may, after concentration has taken place, be returned directly to the oxidation reaction.

At the same time, there is substantial or complete thermal decomposition of the hydrogen peroxide which is present during the distillation of the water/formic acid mixture, representing a great gain in safety. In this way, there is reliable prevention of the undesired formation of hydroperoxides.

However, it may be an additional advantage if the mixture obtained from b) undergoes thermal treatment once again, before c), to decompose any residual hydrogen peroxide or organic hydroperoxides which are still present. This preferably takes place at temperatures from 70 to 100° C., particularly preferably at about 80° C., and with residence times of about one hour at this temperature.

It is possible to employ, according to the invention, both linear and branched monoolefins or monoolefin alcohols. It also possible to employ, where appropriate, mixtures of isomers, which may also have further substituents which are inert under the reaction conditions. Mixtures of isomers are employed, for example, when the resulting mixtures of isomeric diol or triol products can be used directly (i.e., without isomer separation).

Preference is given to the use, in a1), of 2,4,4-trimethyl-1-pentene, 2,4,4-trimethyl-2-pentene, mixtures of the two isomers, 1-pentene, 1-hexene, 1-octene and 1-dodecene. Preference is given, in a2), to the use of 3-buten-1-ol, 5-hexen-1-ol or 9-decen-1-ol. Preferably employed in a2) are at least 2 mole equivalents of formic acid. Particularly preferably, use is made of 4 to 10 mole equivalents of formic acid. This ensures that the free hydroxy group is, for the most part, esterified with formic acid, with proportionate liberation of water. Esterification, moreover, protects from unwanted oxidation reactions in the subsequent reaction with hydrogen peroxide. In this way, a maximum yield and purity of the products is subsequently achieved.

During the addition of the formic acid to the alkenol there is formation of the corresponding alkenyl formate, and the conversion achieved depends greatly on the formic acid: alkenol molar ratio. This dependency is exemplified in the case of 5-hexen-1-ol. formic acid: 5-hexen-1-ol molar ratios (=V), and conversion percentages, were as follows:

| | |
|---|---|
| V = 1:1 | conversion 52% |
| V = 2:1 | conversion 86% |
| V = 4:1 | conversion 96% |
| V = 10:1 | conversion >99% |

The conversion of alkenol to alkenyl formate has a great influence on the formation of subsidiary components in the subsequent oxidation stage, and thus, on the overall yield. A higher alkenol conversion means the formation of fewer subsidiary components and a greater increase in the overall yield.

It is preferred, according to the invention, for the reaction with hydrogen peroxide and formic acid (oxidation of the double bond) in a1), or for the second stage of a2), to be carried out at temperatures ranging from 40 to 120° C., particularly preferably from 50 to 80° C.

After completing the metering of $H_2O_2$, the reaction can be completed in an after-reaction time of from 0.5 to 10 hours, preferably from 1 to 2 hours, at the previously set reaction temperature.

The hydrogen peroxide employed in this case in both a1) and in a2), is preferably in the form of a 30-70% strength aqueous solution, and particularly preferably in the form of a 50-70% strength aqueous solution.

In order to avoid formation of a peroxide depot if the reaction is not carried out continuously, the $H_2O_2$ metering can take place in 4 to 10 hours, preferably within 5 to 7 hours. The peroxide content in the reactor is preferably kept at <10% during the metering time. The total amount of hydrogen peroxide required for the reaction depends on the nature of the reactor. In a reactor with a smooth surface (e.g. glass) an alkene or alkenol: $H_2O_2$ molar ratio of 1:1.2 is sufficient. A larger excess is necessary in reactors with a rough surface because of partial decomposition of $H_2O_2$.

The reaction is carried out on the semi-industrial and industrial scale preferably in a reactor with a smooth surface, for example made of enamel. It is additionally advantageous for the reactor to be adequately passivated before the oxidation reaction. This can be achieved, for example, by methods known to the skilled worker, such as treatment with phosphoric acid or carrying out a first oxidation reaction whose products are not utilized further. It is possible in this way to reduce further the losses of hydrogen peroxide through decomposition in the following batches.

The removal of water and formic acid by distillation in b) is preferably carried out under a pressure ranging from 100 mbar to 1 bar and at a bottom temperature ranging from 20 to 150° C., but particularly preferably under a pressure ranging from 200 mbar to 800 mbar and at a bottom temperature ranging from 60 to 120° C.

The mixture can be concentrated further by methods known to the skilled worker, and the formic acid in particular can be returned to the oxidation reaction. No formic ester is present in this case, resulting in a marked simplification of the workup, for example compared with DE 197 43 015.

The aliphatic $C_1$-$C_4$-alcohol employed in c) is preferably methanol, ethanol, n-propanol, isopropanol, n-butanol, sec-butanol or tert-butanol. All of these alcohols can be obtained at reasonable cost and in various purities and can therefore be variously employed depending on the required product specification. In addition, the alcoholysis reaction takes places according to the invention with these alcohols in a rapid and efficient manner.

Ethanol, n-propanol and/or isopropanol, which have a comparatively low toxicity, are particularly preferably employed. Ethanol is very particularly preferably employed, in which case it is also relatively uncritical for traces possibly to remain in the final product, and the expenditure on purification can be correspondingly less.

The invention can employ both arylsulfonic acids and alkylsulfonic acids.

Preferred arylsulfonic acids have the formula $R_n$Ar—$SO_3H$ in which Ar is phenyl or naphthyl radical. Preferably benzenesulfonic acid, p-toluenesulfonic acid and/or Marlon AS3 acid are employed. Marlon AS3 acid (CAS No.: 85536-14-7) is very particularly preferably employed and represents a benzenesulfonic acid which is substituted in position 4 of the secondary $C_{10-13}$-alkyl radicals and has the following formula

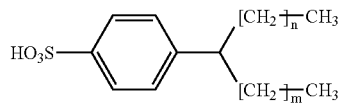

where m+n=7 to 10.

Preferred alkylsulfonic acids are hexanesulfonic acid and/or dodecanesulfonic acid.

Through use of these acids it is possible to afford a fast and efficient transesterification reaction as well as to provide final products which are virtually or completely odorless. This is novel and surprising and represents an exceptional advantage, because the use of the vicinal diols or triols prepared according to the invention in the cosmetics industry is made possible for the very first time in this way.

The catalyst in c) is preferably used in an amount of from 0.005 to 1 mol %, preferably from 0.01 to 0.30 mol %, based on the amount of monoolefin or monoolefin alcohol employed. The optimal concentration can easily be established by the skilled worker depending on the other limiting conditions.

The transesterification reaction with at least one $C_1$-$C_4$-alcohol in c), and the removal of the formic ester, preferably take place at a bottom temperature of from 40 to 160° C., particularly preferably at a bottom temperature of from 50 to 110° C., very particularly preferably at a bottom temperature of from 60 to 90° C. Even at temperatures in the upper preferred range, the products obtained in the process of the invention have no disadvantageous odor properties. Temperatures which are as low as possible in the reaction and/or distillation of the formed alkyl formate are advantageous because it is possible in this case to reduce even further the tendency for odor to be formed.

When the transesterification is carried out discontinuously it is advantageous for the formate intermediates obtained in b) and the catalyst to be mixed, for the mixture to be adjusted to the desired reaction temperature depending on the alcohol used, and for the alcohol to be fed into the lower part of the reactor. The alkyl formate produced in this case is taken off together with excess alcohol as distillate from a distillation apparatus. The progress of conversion is followed by suitable measurement methods (e.g. by gas chromatography or saponification value), and the reaction is terminated at a conversion which is >90%, but particularly preferably >99%.

In order to obtain a very pure final product it is advantageous: 1) for the residue obtained after d) to be neutralized with the aid of an alkali metal alcoholate of an aliphatic $C_1$- to $C_4$-alcohol, preferably sodium methoxide, sodium ethoxide, potassium methoxide or potassium ethoxide, or with the aid of an alkali metal hydroxide, 2) for alcohol or alcohol and/or water to be stripped off by applying vacuum, and 3) for the vicinal alkanediol or alkanetriol remaining in the residue to be isolated by distillation and, where appropriate, purified. If necessary, further purification of the formed diols or triols takes place preferably by distillation. In order to minimize the thermal stress on the target products, a continuous distillation is preferred, for example in a falling film, thin-film or short-path evaporator. Excellent qualities are obtained in this case, the products are moreover virtually or completely odorless, and the products are thus directly suitable for cosmetic applications.

It is advantageous according to the invention for the formic acid/water mixture resulting from the distillation in b) to be concentrated to a desired concentration of from 50 to 100% formic acid and be reused in the reaction in a1) or a2).

It is likewise advantageous for the alcohol to be removed from the formic ester/alcohol mixture resulting from the distillation in d) and reused in c).

The process of the invention can be carried out either continuously or non-continuously. It is particularly advantageous in this connection that the transesterification in c) and the removal by distillation in d) to be carried out continuously.

It is possible with the aid of the process of the invention to obtain alkanediols or alkanetriols of high purity and free of odor. Moreover, the purities achieved after distillation of the diols or triols are >99.0% and even >99.5%.

A great advantage of the process of the invention is that it is very simple to carry out and can be carried out with apparatuses customary in the industry. Moreover, only comparatively small amounts of auxiliaries such as alcohol or acid need to be employed and, in addition, can also be easily removed and, where appropriate, regenerated and recycled.

The process of the invention makes it possible for the very first time for diols and triols to be purified by distillation with commercially acceptable expenditure to give high purities and a virtually or completely odorless quality. The product diols and triols can thus be utilized for cosmetic applications.

The vicinal alkanediols and alkanetriols which can be prepared by the process of the invention are therefore outstandingly suitable for use as ingredient of a cosmetic formulation, for example, as a moisturizer in creams. The invention therefore also relates to the use of vicinal alkanediols and alkanetriols prepared by the process described above in cosmetic formulations, especially as moisturizers, in creams in combination with an excipient, filler, emulsifier, or other cosmetically acceptable ingredient. The examples detailed below are intended to explain the invention further but not restrict it.

EXAMPLES

The present invention is described by way of example in the examples hereinafter. Obviously, numerous modifications and variations of the present invention are possible in light of the above teachings. It is therefore to be understood that, within the scope of the appended claims, the invention may be practiced otherwise than as specifically described herein.

In the following examples, unless otherwise stated, ° C. stands for degrees Celsius, m stands for meter, l stand for liter, g stands for grams, and Pa stands for Pascals.

Example 1

1,2,6-Hexanetriol 450 g (4.22 mol) of 5-hexen-1-ol (94% pure technical product) were introduced into a 2 l jacketed glass reactor with glass stirrer, dropping funnel for metering $H_2O_2$, 0.5 m-long packed column, dephlegmator, condenser, distillate receiver and attached off-gas measurement. At room temperature, 1059 g (23.0 mol) of HCOOH were added, and the mixture was adjusted to 55° C. and kept at 55° C. for 1 hour. Then 373 g (5.0 mol) of hydrogen peroxide (50% strength aqueous solution) were metered in over the course of 6 hours. The reaction proceeded in an exothermic manner. The reactor temperature was kept in the range of from 55° C. to 58° C., with the reaction conducted, for the most part, at a temperature of 55° C. After an after-reaction time of about 3 hours, the reaction was complete; conversion was checked by gas chromatography.

During the peroxide metering and after-reaction, <0.5 l of off-gas (mainly $O_2$) were produced. The peroxide concentration of the reaction solution at this time was about 1.5%. The highest peroxide concentration, 2.5 to 3.5%, was measured at the end of the peroxide metering.

To destroy peroxides, the reactor contents were heated to 80° C. and kept at this temperature for 1 hour. About 10 l of off-gas (mainly $O_2$) were produced, and the peroxide content fell to <0.1% at the end of the hour.

Water pump vacuum was then applied to strip off $H_2O$/HCOOH from the reaction mixture, during which the peroxide concentration fell further (<0.05%). The remaining bottom product (1019 g) was a mixture of alkanetriol mono-, di- and triformates. For the transesterification, the bottom product was mixed with 3.8 g (0.012 mol) of Marlon AS3 acid and 764 g of methanol and heated to 60-70° C. The methyl formate produced thereby was taken off with excess methanol as distillate under atmospheric pressure. The formate conversion was virtually complete after a residence time of 4 hours (saponification value:>99.5% ester conversion). The catalyst was then neutralized by adding 2.8 g of NM30 (30% strength methanolic sodium methoxide solution), and remaining methanol was stripped off by raising the reactor temperature to 82° C. and reducing the pressure to 500 hPa.

Subsequent workup by distillation took place under mild distillation conditions with a maximum bottom temperature of 220° C. The main fraction of 476 g which was obtained was virtually odorless, clear and colorless and had a 1,2,6-hexanetriol content of >99%. The yield of pure product was 84% of theory based on 5-hexen-1-ol employed. The overall yield including the 1,2,6-hexanetriol present in intermediate fractions was 92% of theory. The intermediate fractions were collected after several repetitions and distilled anew, again resulting in pure 1,2,6-hexanetriol. It was thus possible to increase the yield of isolated pure product, calculated over all batches, to close to the predicted theoretical yield.

Example 2

1,2,6-Hexanetriol

The hexanetriol ester mixture was prepared in accordance with Example 1. However, for the subsequent transesterification, 1653 g of n-butanol were employed instead of methanol, and the reaction was carried out at 125° C.-130° C. in 5 hours. The subsequent workup took place in accordance with Example 1, and a main fraction of comparable product quality and 1,2,6-hexanetriol yield was obtained.

Example 3

1,2,6-Hexanetriol (not According to the Invention)

The hexanetriol ester mixture was prepared in accordance with Example 1. For the transesterification with methanol, 0.004 mol of sulfuric acid was employed as catalyst instead of Marlon AS3 acid. The subsequent workup resulted in a main fraction of 1,2,6-hexanetriol which was >99% pure but had a pungent odor.

Example 4

1,2-Hexanediol 242 g (2.87 mol) of 1-hexene were reacted with 330 g of formic acid (7.17 mol) and 232 g (3.41 mol) of a 50% strength aqueous $H_2O_2$ solution as in Example 1. However, in this case, the hydrogen peroxide metering was started immediately after the addition of formic acid and adjustment of the reactor temperature (the reaction temperature ranged from 55° C. to 60° C. with the reaction conducted, for the most part, at a temperature of 55° C.). The reaction was carried out over the course of 6 hours. After the $H_2O_2$ metering and after-reaction (3 hours at 55° C.), the removal of $H_2O$/HCOOH by distillation was carried out directly at 70° C.-138° C. under water pump vacuum.

The transesterification was carried out in the presence of 0.001 mol of Marlon AS3 acid and with 400 g of methanol at 55° C.-85° C. in 3 hours and, after the workup by distillation, the main fraction obtained was >99.5% pure, virtually odorless 1,2-hexanediol. The 1,2-hexanediol yield based on 1-hexene employed was: 92% of theory (overall) or 80% of theory (pure product).

Summary of conditions of different stages of the process (Temperature/Time):

| Reaction with H$_2$O$_2$ (metering): | 55° C.-60° C./6 hours |
|---|---|
| After-reaction: | 65° C./3 hours |
| H$_2$O/HCOOH removal under vacuum: | 70° C.-138° C. |
| Transesterification: | 55° C.-85° C./3 hours |

Example 5

1,2-Octanediol 314 g (2.80 mol) of 1-octene were reacted with 330 g (7.17 mol) of formic acid and 232 g (3.41 mol) of a 50% strength aqueous H$_2$O$_2$ solution in accordance with Example 4. 575 g of ethanol were employed for the Marlon AS3 acid-catalyzed transesterification, and the main fraction obtained after the workup by distillation was >99.5% pure, virtually odorless 1,2-octanediol.

The 1,2-octanediol yield based on 1-octene employed was: 85% of theory (overall) or 75% of theory (pure product).

Summary of conditions of different stages of the process (Temperature/Time):

| Reaction with H$_2$O$_2$ (metering): | 55° C./6 hours |
|---|---|
| After-reaction: | 65° C./3 hours |
| H$_2$O/HCOOH removal under vacuum: | 65° C.-110° C. |
| Transesterification: | 75° C.-85° C./3 hours |

Example 6

1,2-Dodecanediol 336 g (2.00 mol) of 1-dodecene were reacted with 236 g of formic acid and 185 g of a 50% strength aqueous H$_2$O$_2$ solution in accordance with Example 4. 412 g of ethanol were employed for the Marlon AS3 acid-catalyzed transesterification, and the main fraction obtained after the workup by distillation was 99.5% pure, virtually odorless 1,2-dodecanediol.

The 1,2-dodecanediol yield based on 1-dodecene employed was:
82% of theory (overall) or 74% of theory (pure product).

Summary of conditions of different stages of the process (Temperature/Time):

| Reaction with H$_2$O$_2$ (metering): | 55° C./8 hours |
|---|---|
| After-reaction: | 65° C./3 hours |
| H$_2$O/HCOOH removal under vacuum: | 65° C.-115° C. |
| Transesterification: | 75° C.-85° C./3 hours |

Example 7

1,2,4-Butanetriol 72.1 g (1.00 mol) of 3-buten-1-ol were reacted with 120 g (2.61 mol) of formic acid and 82 g (1.21 mol) of 50% strength aqueous H$_2$O$_2$ solution in accordance with Example 1. 100 g of methanol were employed for the Marlon AS3 acid-catalyzed transesterification, and the main fraction obtained after the workup by distillation was >96.3% pure, virtually odorless 1,2,4-butanetriol.

The 1,2,4-butanetriol yield based on 3-buten-1-ol employed was:
72% of theory (overall) or 70% of theory (pure product).

Summary of conditions of different stages of the process (Temperature/Time):

| Esterification of 3-buten-1-ol + HCOOH: | 55° C./1 hour |
|---|---|
| Reaction with H$_2$O$_2$ (metering): | 55° C.-60° C./4 hours |
| After-reaction: | 55° C./2 hours |
| Peroxide decomposition: | 80° C./2 hours |
| H$_2$O/HCOOH removal under vacuum: | 65° C.-115° C. |
| Transesterification: | 55° C.-85° C./3 hours |

Example 8

1,2-Dodecanediol (Comparative, According to DE 197 43 015, Example 6, not According to the Invention)

168.3 g (1.0 mol) of 1-dodecene and 73.6 g (1.6 mol) of formic acid were mixed. This mixture was heated to 100° C. and then 115.7 g (1.7 mol) of 50% strength hydrogen peroxide solution were added dropwise over a period of 2 hours. The mixture was then stirred at 100° C. for 45 min. 64.1 g (2 mol) of methanol and 0.1 g of concentrated sulfuric acid were added, and the mixture was heated under reflux for 30 min and then the methyl formate, methanol and water were removed by distillation under atmospheric pressure. A >99% pure main fraction was isolated after the subsequent workup by distillation. The freshly distilled target product had an unpleasant, pungent odor.

The 1,2-dodecanediol yield based on 1-dodecene employed was:
81% of theory (overall) or 73% of theory (pure product).

Example 9

1,2,6-Hexanetriol

The hexanetriol ester mixture was prepared in accordance with Example 1. For the subsequent transesterification with ethanol (1098 g), 2 g (0.012 mol) of hexanesulfonic acid were employed instead of Marlon AS3 acid as catalyst. The subsequent workup took place in accordance with Example 1, and a main fraction with comparable product quality and yield of 1,2,6-hexanetriol was obtained.

Example 10

1,2,6-Hexanetriol

The hexanetriol ester mixture was prepared in accordance with Example 9. For the subsequent transesterification with ethanol, 3.2 g (0.012 mol) of dodecanesulfonic acid were employed instead of hexanesulfonic acid as catalyst. The subsequent workup took place in accordance with Example 9, and a main fraction with comparable product quality and yield of 1,2,6-hexanetriol was obtained.

The above written description of the invention provides a manner and process of making and using it such that any person skilled in this art is enabled to make and use the same, this enablement being provided in particular for the subject matter of the appended claims, which make up a part of the original description.

As used above, the phrases "selected from the group consisting of," "chosen from," and the like include mixtures of the specified materials.

All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out. Terms such as "contain(s)," and the like as used herein are open terms meaning 'including at least' unless otherwise specifically noted.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

The invention claimed is:

1. A process for preparing a vicinal alkanediol or an alkanetriol comprising
   a1) reacting at least one monoolefin comprising 4 to 20 carbon atoms with hydrogen peroxide and formic acid in the presence of water to form a mixture or
   a2) reacting at least one monoolefin alcohol comprising 4 to 20 carbon atoms first with formic acid, and then reacting the product formed thereby with hydrogen peroxide in the presence of water to form a mixture,
   b) removing, by distillation, the water and formic acid from the mixture obtained in a1) or a2),
   c) reacting the mixture obtained from b) with at least one aliphatic $C_1$-$C_4$-alcohol in the presence of at least one arylsulfonic acid, at least one alkysulfonic acid, or a combination thereof to form the vicinal alkanediol or the alkanetriol and at least one formic ester by-product, wherein the at least one arylsulfonic acid is of the formula $R_n Ar$—$SO_3H$, wherein R may be identical or different and is a linear or branched $C_1$- to $C_{19}$-alkyl radical, fluorine or chlorine, Ar is a phenyl, naphthyl, anthryl or phenanthryl radical, and n can be 0, 1, 2 or 3, and
   wherein the at least one alkylsulfronic acid is a $C_6$- to $C_{16}$-alkylsulfonic acid; and
   d) optionally removing, by distillation, the at least one formic ester by-product formed together with any residual at least one aliphatic $C_1$-$C_4$-alcohol to isolate the vicinal alkanediol or the alkanetriol.

2. The process of claim 1, wherein d) is carried out, and wherein c) and d) are carried out simultaneously.

3. The process of claim 1, wherein d) is carried out, and wherein c) and d) are carried out successively.

4. The process of claim 1, wherein a1) is carried out, and wherein the at least one monoolefin is selected from the group consisting of 2,4,4-trimethyl-1-pentene, 2,4,4-trimethyl-2-pentene, 1-pentene, 1-hexene, 1-octene, 1-dodecene and mixtures thereof.

5. The process of claim 1, wherein a2) is carried out, and wherein the at least one monoolefin alcohol is selected from the group consisting of 3-buten-1-ol, 5-hexen-1-ol, 9-decen-1-ol, and mixtures thereof.

6. The process of claim 1, wherein a2) is carried out, and wherein at least 2 mole equivalents of formic acid are employed in a2).

7. The process of claim 1, wherein a1) is carried out, and wherein a1) is conducted at a temperature ranging from 40 to 120° C.

8. The process of claim 1, wherein the hydrogen peroxide employed in a1) or in a2) is a 30-70% strength aqueous solution.

9. The process of claim 1, wherein the removal of water and formic acid by distillation in b) is carried out under a pressure of from 100 mbar to 1 bar and at a bottom temperature of from 20 to 150° C.

10. The process of claim 9, wherein the removal of water and formic acid by distillation in b) is carried out under a pressure of from 200 mbar to 800 mbar and at a bottom temperature of from 60 to 120° C.

11. The process of claim 1, wherein the mixture obtained from b) is thermally treated before c).

12. The process of claim 1, wherein the least one aliphatic $C_1$-$C_4$-alcohol in c) is selected from the group consisting of methanol, ethanol, n-propanol, isopropanol, n-butanol, sec-butanol, tert-butanol, or a combination thereof.

13. The process of claim 12, wherein ethanol, n-propanol, isopropanol or a combination thereof are employed.

14. The process of claim 1, wherein the at least one arylsulfonic acid is present, and wherein the at least one arylsulfonic acid is selected from the group consisting of benzenesulfonic acid, p-toluenesulfonic acid, Marlon AS3 acid, and a combination thereof.

15. The process of claim 1, wherein the at least one alkysulfonic acid is present, and wherein the at least one alkylsulfonic acid is selected from the group consisting of hexanesulfonic acid, dodecanesulfonic acid, and a combination thereof.

16. The process of claim 14, wherein Marlon AS3 acid is employed as the at least one arylsulfonic acid.

17. The process of claim 1, wherein the amount of catalyst used in c) is from 0.005 to 1 mol % based on the amount of the at least one monoolefin or the at least one monoolefin alcohol employed.

18. The process of claim 1, wherein d) is carried out, and wherein the reacting in c) and the removing in d) take place at a bottom temperature of from 40° C. to 160° C.

19. The process of claim 18, wherein d) is carried out, and wherein the reacting in c) and the removing in d) take place at a bottom temperature of from 50° C. to 110° C.

20. The process of claim 1, wherein d) is carried out, and wherein the vicinal alkanediol or the alkanetriol obtained from d) is neutralized with the aid of an alkali metal alcoholate of an aliphatic $C_1$- to $C_4$-alcohol, an alkali metal hydroxide, alcohol, water, or a combination thereof, and the thus neutralized vicinal alkane diol or the alkanetriol is subsequently purified by distillation.

21. The process of claim 20, wherein the alkali metal alcoholate of an aliphatic $C_1$-to-$C_4$ alcohol is selected from the group consisting of sodium methoxide, sodium ethoxide, potassium methoxide, and potassium ethoxide.

22. The process of claim 1, wherein the formic acid and the water removed by distillation in b) is concentrated to a desired concentration of from 50 to 100% formic acid and is reused in the reaction in a1) or a2).

23. The process of claim 1, wherein d) is present, and wherein the at least one aliphatic $C_1$-$C_4$ alcohol removed by the distillation in d) and is reused in c).

* * * * *